(12) United States Patent
Roche Rebollo

(10) Patent No.: US 10,507,304 B2
(45) Date of Patent: Dec. 17, 2019

(54) CATHETER DEVICES, KITS AND METHODS

(71) Applicant: Vascular Barcelona Devices, S.L., Barcelona OT (ES)

(72) Inventor: Enrique Roche Rebollo, Barcelona (ES)

(73) Assignee: VASCULAR BARCELONA DEVICES, S.L., Barcelona (ES)

( * ) Notice: Subject to any disclaimer, the term of this patent is extended or adjusted under 35 U.S.C. 154(b) by 204 days.

(21) Appl. No.: 15/415,533

(22) Filed: Jan. 25, 2017

(65) Prior Publication Data

US 2017/0128700 A1 May 11, 2017

Related U.S. Application Data

(63) Continuation of application No. PCT/EP2014/079311, filed on Dec. 24, 2014.

(30) Foreign Application Priority Data

Jul. 29, 2014 (ES) .................................. 201431141

(51) Int. Cl.
*A61M 25/06* (2006.01)
*A61B 17/3209* (2006.01)
(Continued)

(52) U.S. Cl.
CPC ... *A61M 25/0606* (2013.01); *A61B 17/32093* (2013.01); *A61B 17/3415* (2013.01);
(Continued)

(58) Field of Classification Search
CPC ............ A61M 25/0028; A61M 25/065; A61M 25/0606; A61M 25/0023; A61M 25/01;
(Continued)

(56) References Cited

U.S. PATENT DOCUMENTS 4,629,450 A * 12/1986 Suzuki .............. A61M 25/0606
604/104
4,929,246 A * 5/1990 Sinofsky ............ A61B 17/0057
606/15

(Continued)

FOREIGN PATENT DOCUMENTS

DE 10100332 A1 7/2002
WO 0110345 A1 2/2001

(Continued)

OTHER PUBLICATIONS

International Search Report and Written Opinion in corresponding International Application No. PCT/EP2014/079311, dated May 15, 2015.

*Primary Examiner* — Nilay J Shah
(74) *Attorney, Agent, or Firm* — Edell, Shapiro & Finnan, LLC

(57) ABSTRACT

A catheter device configured to provide access to a hollow organ is provided. It includes a body extending longitudinally from a proximal end to a distal end and a flexible insertion tube extending longitudinally from a proximal end to a distal end, wherein the body includes an elongated channel along the longitudinal length of the body extending from the proximal end of the body to the distal end of the body, wherein the channel is configured to receive an elongate needle. The body further comprises one or more cutting edges extending rearwardly from a distal end of the body. Furthermore, the flexible insertion tube of the catheter device is coupled to the distal end of the body and comprises a tubular elongated passage aligned with the tubular elongated channel of the body forming a lumen. Kits including such catheter devices and methods for accessing a hollow organ are also provided.

19 Claims, 6 Drawing Sheets

(51) Int. Cl.
  *A61B 17/34* (2006.01)
  *A61M 25/00* (2006.01)
  *A61M 25/01* (2006.01)
  *A61B 17/32* (2006.01)
(52) U.S. Cl.
  CPC .... *A61M 25/0023* (2013.01); *A61M 25/0105* (2013.01); *A61M 25/065* (2013.01); *A61B 2017/320052* (2013.01); *A61M 25/0662* (2013.01)
(58) Field of Classification Search
  CPC ....... A61M 2025/0687; A61B 17/3209; A61B 17/32093; A61B 17/3211; A61B 2017/32113; A61B 5/150458
  See application file for complete search history.

(56) References Cited

U.S. PATENT DOCUMENTS

| | | | |
|---|---|---|---|
| 4,955,890 A | 9/1990 | Yamamoto et al. | |
| 5,693,030 A * | 12/1997 | Lee | A61M 25/0068 604/117 |
| 5,807,317 A * | 9/1998 | Krech, Jr. | A61B 17/3415 604/272 |
| 2002/0040231 A1 | 4/2002 | Wysoki | |
| 2004/0030319 A1* | 2/2004 | Korkor | A61M 25/0662 604/506 |
| 2009/0143808 A1* | 6/2009 | Houser | A61B 17/0057 606/170 |
| 2009/0254038 A1* | 10/2009 | Lapeyre | A61B 17/3417 604/164.01 |
| 2011/0137395 A1 | 6/2011 | Fargahi | |
| 2013/0178711 A1* | 7/2013 | Avneri | A61B 17/12109 600/208 |

FOREIGN PATENT DOCUMENTS

| | | |
|---|---|---|
| WO | 2007035889 A2 | 3/2007 |
| WO | 2014027268 A1 | 2/2014 |

* cited by examiner

PRIOR ART

CATHETER DEVICES, KITS AND METHODS

CROSS REFERENCE TO RELATED APPLICATIONS

This application is a continuation of International Application PCT/EP/2014/079311, filed on Dec. 24, 2014, which claims priority under 35 U.S.C. § 119 to Application No. ES P201431141 filed on Jul. 29, 2014, the entire contents of which are hereby incorporated by reference.

FIELD OF THE INVENTION

The present disclosure relates to catheter devices configured to provide access to hollow organs. The present disclosure further relates to kits including such catheter devices and methods for using catheter devices, in particular for accessing hollow organs. Hollow organs, as used herein explicitly include bodily lumens, e.g. cavities and tubular organs.

BACKGROUND

Medical procedures to obtain access through the patient's skin to hollow organs such as e.g. blood vessels are widely used and for all kinds of interventions, e.g. endovascular repair, angioplasty, insertion of chest drains etc.

One known technique used in such procedures is the Seldinger technique which can be used e.g. for vascular access, or for placement of pleural, peritoneal, cardiac, and enteral drains and tubes. This procedure usually involves the following steps depicted in FIG. 1: A puncture is performed with an introducer needle (or "trocar") 20 placed through the patient's skin and into the hollow organ 21 of concern (step A). A soft-tipped guide wire 22 is then passed through the lumen of the introducer needle 20 and brought into a desired position within the hollow organ 21 (step B). Then, the needle 20 is withdrawn while the guide wire 22 remains in the hollow organ 21 (step C). At this point of the procedure, a guide catheter 23 e.g. a blunt cannula or other devices which allows investigation or treatment of the hollow organ may be passed over the guide wire (step D). Once the guide catheter 23 is placed in the correct position for investigation or treatment of the hollow organ, the wire is removed (step E).

The guiding catheters by necessity are larger than the guide wire over which they are passed and hence cannot pass through the skin via the small hole made by the initial needle puncture, thus an enlargement of the puncture site may be needed. For this reason, a small skin incision is made adjacent to the puncture site i.e. the point of entry of the guide wire into the skin. This enlargement of the puncture site may be made with a sharp instrument e.g. a surgical scalpel. However, this requires great dexterity and it is difficult to make a precise incision. Accidents can occur if the incision is made too deep or too long in case the surgeon does not have a good enough control. This may lead to hemorrhage or perforation of the hollow organ (e.g. vein). In addition, creating and enlarging the puncture site may be time consuming, which increases stress for the patient. There is also the risk of cutting the guide wire, which is a very thin wire. And it also happens that a cut is made which is not exactly at the puncture site.

SUMMARY

It is an object of the present disclosure to provide improved catheter devices, (surgical) kits and methods that at least partially resolve some of the aforementioned problems.

In a first aspect, a catheter device configured to provide access to a hollow organ is provided. The catheter device includes a body extending longitudinally from a proximal end to a distal end and a flexible insertion tube extending longitudinally from a proximal end to a distal end, wherein the body comprises: an elongated channel extending from the proximal end of the body to the distal end of the body, wherein the channel is configured to receive an elongate needle. The body further comprises one or more cutting edges extending rearwardly from a distal end of the body. Furthermore, the flexible insertion tube of the catheter device is coupled to the distal end of the body and comprises a tubular elongate passage aligned with the elongate channel of the body thus forming a lumen.

According to this first aspect, a catheter device that is configured to provide a double function of providing access to a hollow organ and to facilitate the introduction of larger devices is provided. To this end, the catheter device is provided with one or more cutting edges. These cutting edges may enlarge a puncture or a nick previously made in the patient's skin thus the use of supplementary cutting instruments such as scalpels may be avoided. With this arrangement, the risk of accidents manipulating the cutting instrument e.g. a cutting off the guide wire and/or making the nick too deep or too long are also avoided. In addition, the risk of making by mistake a second nick near the first nick instead of enlarging the first nick is also avoided since the incision is made larger by simply guiding the catheter along the guide wire.

The procedure for accessing e.g. a vein through the patient's skin is inherently improved. The catheter with cutting edges as proposed herein may be held and used the same as traditional trocars or Abbocaths ("hollow needle within a tube", typically made of Teflon). In a very similar manner as in the traditional method, the initial puncture may be made. However, unlike prior methods, the needle can then be immediately removed. A guide wire may be introduced into the organ (vein) through the channel in the catheter that previously surrounded the needle. Once in place, the catheter just needs to be advanced a bit along the guide wire in order to increase an incision in a very controlled manner. Since the needle stays in place less time, the risk of an accidental movement by a nurse or other healthcare professional potentially cutting skin or another organ is reduced.

Distal herein is to be understood as a side of an instrument further away from a person (e.g. nurse or doctor) using it. Proximal herein is to be understood as the opposite side.

The catheter may have a variety of shapes. In some examples, the catheter is substantially flat. The cutting edges may extend rearwardly from a distal end of the catheter device and may be substantially straight edges. In other examples, the cutting edges may be curved outwardly. Straight edges provide a constant ratio between axial advancement (of the catheter device) and size of the incision. Edges that are curved outwardly may be more smoothly introduced at the beginning of an incision.

In a further example, a conical cutting edge may be provided. The diameter of the cone may increase from a distal end of the catheter device towards the rear, i.e. towards the proximal end.

In some examples, the one or more cutting edges may comprise consecutive symmetric marks provided at the cutting edges configured to indicate the length of the access into the skin of a patient.

In some examples, the body of the catheter device may be made from a polymer, in particular a polymer that can be sterilized. In preferred examples, the cutting edges and body are integrally formed and made from a suitable polymer. By providing the cutting edge of a polymer instead of more traditional metallic blades, less danger for personnel using the catheter occurs. A catheter could be safely held and no unintentional injury would normally occur.

In a further aspect, a catheter device configured to provide access to a hollow organ is provided. The catheter device includes a body extending longitudinally from a proximal end to a distal end and comprising a through-hole from the proximal end of the body to the distal end of the body, wherein the through-hole is configured to receive an elongate needle. The body further comprises one or more cutting edges extending rearwardly from a distal end of the body. The cutting edges are integrally formed with the rest of the body and are made from a polymer or polymer mixture.

In yet another aspect, a kit is provided. The kit includes a catheter device according to any example of the first aspect. The kit further includes a needle configured to be slidably inserted into the lumen (formed by the passage through the insertion tube and the channel through the body of the catheter device), wherein the needle comprises a cutting end which when inserted in the lumen of the catheter device extends beyond a distal end of the lumen.

In some examples, the needle may be hollow. Potentially a guide wire could thus be passed through the needle. In some examples, a kit may further comprise a guide wire and/or a guide catheter. A surgical kit comprising all or various of the elements needed in procedures for gaining access to a lumen (e.g. a vein or urinary tract) can be provided.

In a further aspect, a method for accessing a hollow organ is provided using a catheter device as previously explained. An elongate needle comprising a cutting end can be inserted into the lumen of the catheter device until the cutting end extends beyond the distal end of the insertion tube of the catheter device. A nick can then be made in the patient's skin using the cutting end of the needle while in the lumen of the catheter device. At least part of the insertion tube can be thus be inserted into the nick and advanced into the hollow organ and a guide wire can be advanced through the lumen of the catheter device. Then, the length of the nick or incision can be increased by inserting the cutting edges of the body into the nick.

In accordance with this aspect, by simply advancing the combination of needle and catheter device, an initial puncture can be made and the insertion tube can enter into the hollow organ. A guide wire can then be introduced, either through a hollow needle, or through the catheter device. By further advancing the catheter device along the guide wire, an incision may be made large so that a sheath, or guide catheter can subsequently be positioned.

BRIEF DESCRIPTION OF THE DRAWINGS

Non-limiting examples of the present disclosure will be described in the following, with reference to the appended drawings, in which.

The FIGS. 4-11 schematically illustrate a sequence of situations that may occur during the performance of a method for accessing a hollow organ.

DETAILED DESCRIPTION

Figure 1:
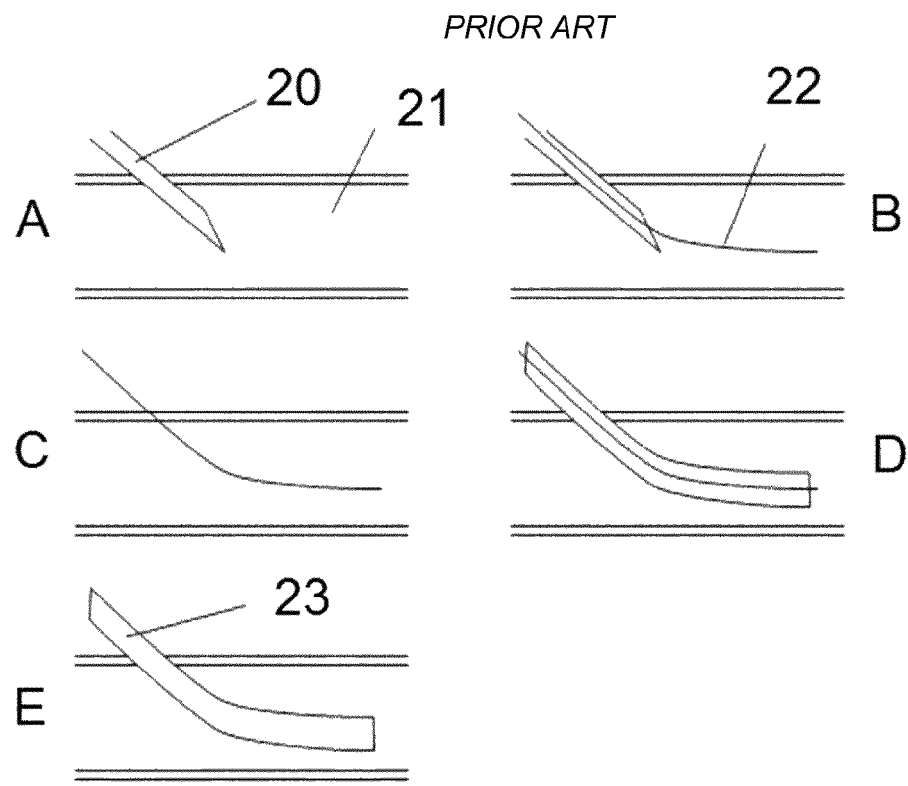
FIG. 1 schematically illustrates a sequence of situations that may occur during the performance of the Seldinger technique.

FIG. 1 showing a prior art technique for accessing a hollow organ has hereinbefore already been discussed.

Figure 2:
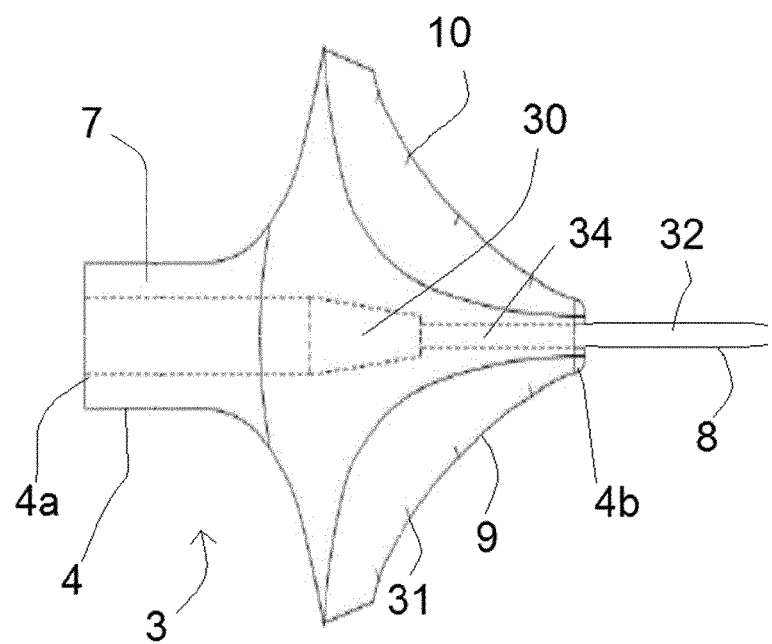
FIG. 2 schematically illustrates a catheter device.

FIG. 2 schematically illustrates a catheter device. The catheter device 3 may comprise a body 4 extending longitudinally from a proximal end 4a (closer to the person handling the catheter) to a distal end 4b (the end further away from the person handling the catheter).

The body 4 may be made of any plastic suitable for any health product e.g. a PVC plastic, a cured epoxy resin, or some other suitable polymer. Such a polymer could be fibre-reinforced in some examples. In some examples, the distal end 4b of the body may be relatively sharp, thus the insertion of the body 4 into the patient's skin and a hollow organ of the patient may be facilitated.

In some other examples, one or more small blades (not shown) may be located at or near the distal end 4b of the body. These small blades may be made of the same material of the body 4 although some other materials may also be possible such a material for surgical scalpel blades, that is, surgical grade stainless steel.

The body 4 may comprise an elongate channel 30 along the longitudinal length of the body extending from the proximal end 4a of the body to the distal end 4b of the body 4. A through-hole is thus formed in the body.

In some examples, the channel 30 may have the same diameter at the proximal end 4a of the body and at the distal end 4b of the body. In some other examples, the channel 30 may have a diameter at or near the proximal end 4a of the body 4 greater than that at or near the distal end 4b of the body 4 such that the diameter of the channel decreases (optionally constantly) along the longitudinal length of the body 4 extending from the proximal end 4a to the distal end 4b. This way, the channel 30 may have the shape of a funnel, thus the operation of, for example, a needle once is inserted into the channel may be improved.

The inner channel 30 may be specifically shaped to provide a seat for a needle of a certain kind or certain brand. The needle in question can thus be inserted in the proximal end of the device and be advanced until it encounters the seat (or "stopper").

The body 4 may comprise a grip 7 located at or near the proximal end 4a of the body, thus the insertion, removal and manipulation of the body 4 (and thus the whole catheter 3) may be improved. The grip 7 may be shaped so that it may be easily held between the fingers of the user/surgeon. The grip 7 may be made of any suitable rough material e.g. plastic polymer, thus the manipulation of the catheter by the user/surgeon may be improved, especially if the grip portion 7 of the catheter 3 is wet, or has saline or body fluids on it. The grip 7 may have a variety of coatings, including e.g. a hydrophilic coating. With this arrangement, the catheter device 3 may be easily manipulated and used with great accuracy.

The body 4 may comprise one or more cutting edges extending rearwardly from a distal end 4b of the body 4. In this particular example, a first cutting edge 9 and a second cutting edge 10 are shown. The first cutting edge 9 and the second cutting edge 10 may be configured to enlarge a nick previously made on the patient's skin using e.g. a needle device. The first cutting edge 9 and the second cutting edge 10 may be made of the same material of the body 4 and may be integrally formed with the rest of the body. In some other examples, the first cutting edge 9 and the second cutting edge 10 may be made of any suitable material for surgical scalpel blades, that is, surgical grade stainless steel. However, other suitable metals, or even biocompatible polymer plastics, could be used for the construction of the first cutting edge 9 and the second cutting edge 10.

The first cutting edge 9 and the second cutting edge 10 are depicted to be substantially curved. This configuration may allow a smooth initial introduction of the first cutting edge 9 (and thus the symmetric second cutting edge 10) into the nick previously made on the patient's skin, thus the accuracy of the enlargement of the nick may be improved.

The first cutting edge 9 and the second cutting edge 10 may be provided with consecutive symmetric marks 31 provided at the first cutting edge 9 and the second cutting edge 10 configured to indicate the length of the access into the patient's skin. These marks 31 may indicate the length of the access into the patient's skin (and thus the hollow organ). Each mark (and its symmetric mark located at the second cutting edge 10) may include a sign in a suitable unit of length e.g. millimetres. For example, the consecutive symmetric marks may be equidistantly spaced apart with respect to each other between 0.5 and 1.5 cm. In some examples, the first cutting edge 9 and/or the second cutting edge 10 may be protected with a cover or a protection device suitable to avoid cuts.

The marks may provide accurate information to the surgeon about the enlargement of the nick, thus the accuracy and the control enlarging the nick may be improved.

A flexible insertion tube 8 may also be provided. The tube may be made of polymers such as Teflon® or Polytetrafluoroethylene (PTFE) which is a synthetic fluoropolymer of tetrafluoroethylene. The flexible insertion tube 8 may be coupled to the distal end 4b of the body (or could alternatively be integrally formed with it).

The flexibility of the tube 8 may help with a better introduction of the tube into the hollow organ. Furthermore, it can reduce the chances of the hollow organ being punctured or otherwise damages e.g. by a sudden or accidental movement. The needle used for initial puncturing can immediately be removed, whereas a guide wire can still be introduced into the lumen of the organ through the proximal side of body 4 and the tube 8.

The flexible insertion tube 8 may comprise a tubular elongate passage 32 that is aligned with the elongated channel 30 of the body 4, thus a lumen 34 may be defined along the flexible insertion tube 8 and the body 4 of the catheter device 3.

Figure 3:
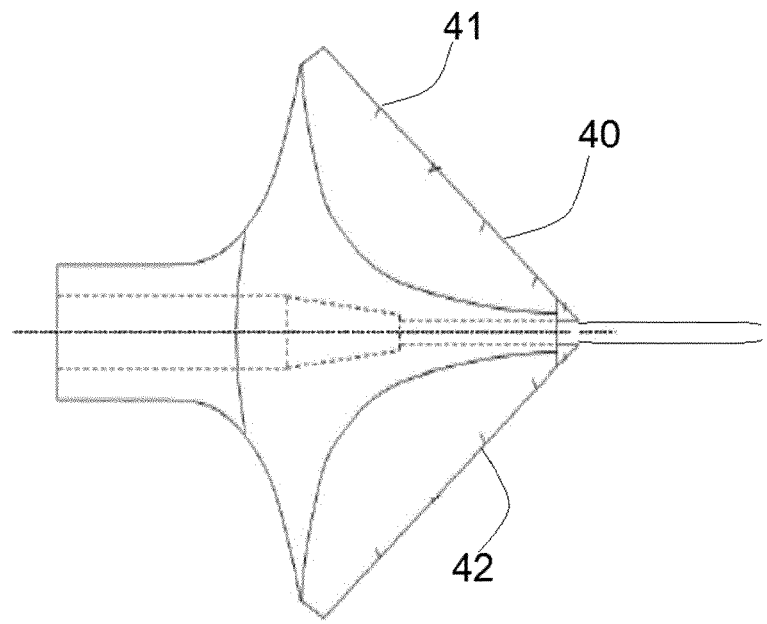
FIG. 3 schematically illustrates another catheter device.

The FIG. 3 schematically illustrates one of the symmetrical parts of another catheter device. In this example, the cutting edge 40 (and its symmetric cutting edge 42) may be substantially straight, thus a homogeneous control regarding the speed and the length of the enlargement of the nick previously made may be achieved. The cutting edge 40 may also in this case be provided with consecutive symmetric marks 41 provided at the cutting edge 40 configured to indicate the length of the access into the patient's skin (and thus the hollow organ). These marks 41 may indicate the length of the access into patient's skin. The remainder of the structure of the catheter device may be substantially the same as described in FIG. 2.

In both illustrated examples, the body of catheter device is substantially flattened on a top side and bottom side, which offers some advantages in handling and gripping of the catheter. The catheter device may thus be held in a manner that can be very similar to the way needles (with suitable sheaths or cover tubes) are being held by personnel. For example, and in accordance with a nurse's or doctor's preference, the body of the catheter device may be held between an index finger and a middle finger. A thumb of the same hand may be used to push against the back of the catheter device and thus push it forwards. It should be clear that the body does not need to be substantially flattened, but that other shapes are possible.

Also in both examples so far, the catheter devices are substantially arrow shaped (with an insertion tube at the apex of the arrow), but alternative shapes are possible while providing one or more suitable cutting edges.

In the examples of FIGS. 2 and 3, two small protrusions are provided at the distal end of the body for facilitating the entry of the body (and the cutting edges) into an initial skin nick. These two small protrusions are optional so that they may not be there in other examples.

FIGS. 4-11 schematically illustrate a sequence of situations that may occur during the performance of a method for accessing a hollow organ according to an example. Same reference numbers denote the same elements. The method is described below with reference to the sequences of situations illustrated by FIGS. 4-11.

Figure 4:
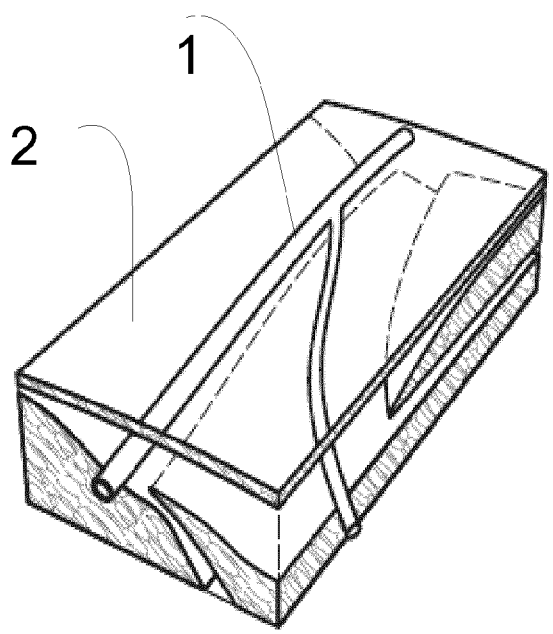

In FIG. 4, a hollow organ 1 e.g. a blood vessel may be seen that is located under a patient's skin 2.

Figure 5:
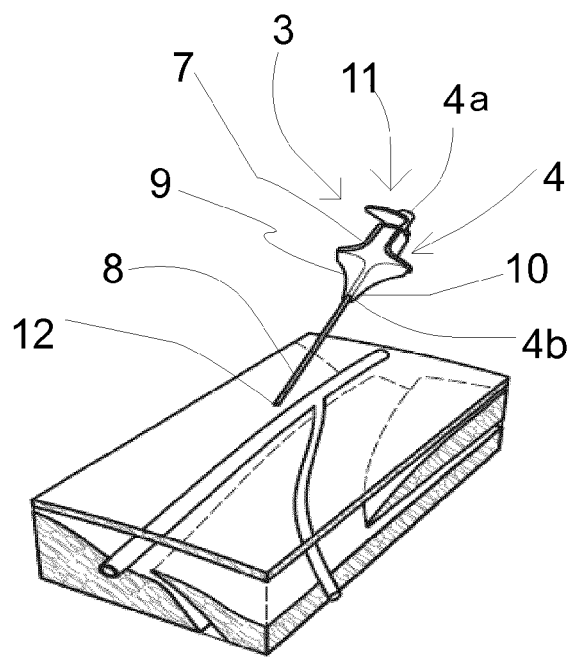

In FIG. 5, an example of a catheter device 3 similar to the previous examples is shown.

The body 4 may comprise one or more cutting edges extending rearwardly from a distal end of the body, in this particular example a first cutting edge 9 and a second cutting edge 10 are provided opposite to each other.

A flexible insertion tube 8 is also shown. The structure of the flexible insertion tube 8 may also be the same as described in the FIG. 2.

The removable elongate needle 11 may comprise a cutting end 12 and at the opposite end a handle or grip can be foreseen. The needle 11 may thus be inserted or withdrawn along the lumen defined by the through-hole defined in body 4, and the insertion tube.

The removable elongated needle 11 may be a hollow needle comprising a passage configured to allow the insertion and removal of a wire through the passage (and thus through the needle and the lumen). The removable elongated needle 11 may have diameter in the range e.g. 21 to 27 gauges preferably 23 to 25 gauges depending on the expected uses of the catheter 3.

The elongate needle 11 could be pre-assembled with the catheter device, thus forming a pre-assembled kit. Alternatively, the needle 11 and the catheter device 3 can be delivered separately as a set of parts, in which case a surgeon or nurse assembles the removable elongated needle 11 on the catheter device 3 in preparation for use.

The FIG. 5 illustrates an initial situation. The cutting end 12 of the elongated needle 11 extends beyond the distal end of the lumen (and thus the distal end of the flexible insertion tube 8). This way, the cutting end 12 (and thus the catheter 3) is ready to puncture the patient's skin and enter into the vein.

Figure 6:
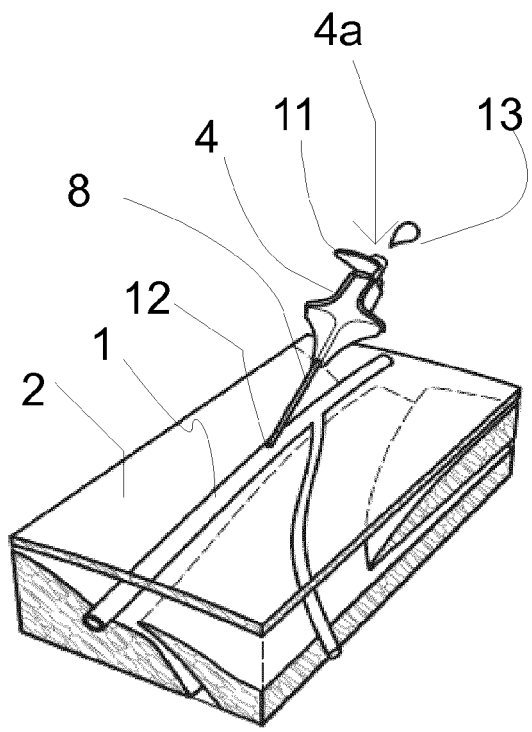

In FIG. 6, the cutting end 12 of the removable elongated needle 11 may be brought near the patient's skin 2. Once situated at the desired position, the needle can be used to puncture the skin. The cutting end 12 of the removable elongated needle 11 may be advanced into the vein 1 until part of the flexible insertion tube 8 is also introduced into the hollow organ 1. Once the removable elongated needle 11 reaches the vein, blood 13 may drip out at a proximal end of the catheter (e.g. the proximal end of a hollow needle), thus indicating the user/surgeon that the needle 11 (and thus the flexible insertion tube 8) has been properly placed into the hollow organ 1.

Figure 7:
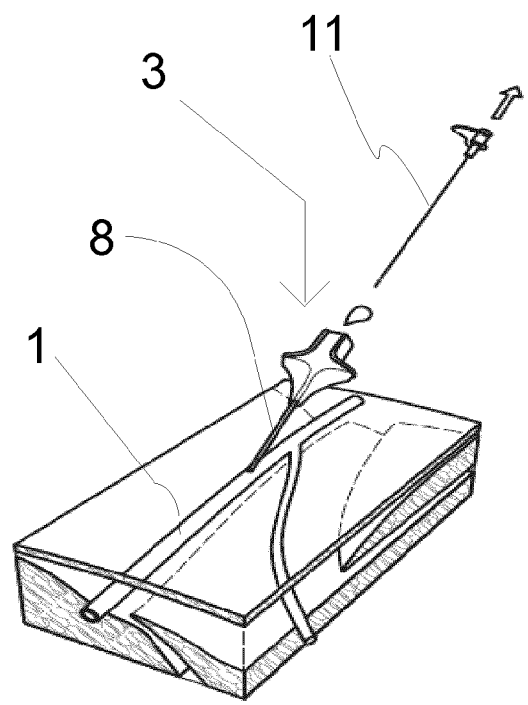

In FIG. 7, the flexible insertion tube 8 has already been introduced and properly placed in vein 1. This way, the needle 11 may thus be withdrawn along the lumen of the catheter device 3 in the direction of the arrow while the flexible insertion tube 8 is left in the desired position. This way, only the flexible insertion tube 8 is located and properly allocated in the hollow organ 1.

In alternative examples, the needle may be a hollow needle and the fact that the needle is hollow can be used to introduce a guide wire therethrough.

Figure 8:
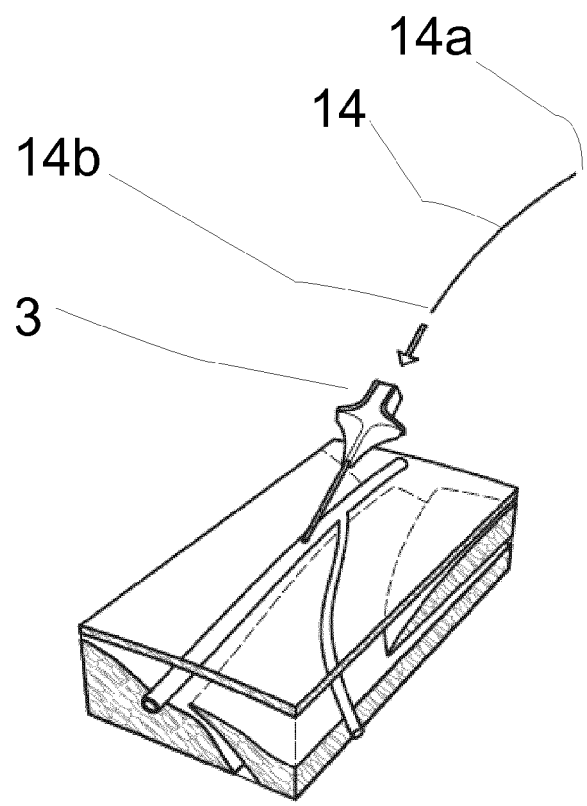

In FIG. 8, a guide wire 14 configured to be slidably inserted and removed through a passage or a lumen may be provided. In this particular example, the guide wire 14 is inserted through the lumen of the catheter 3. The guide wire 14 may have a suitable diameter in order to be inserted into the lumen in the direction pointed by the arrow. The guide wire 14 can further have a very low coefficient of friction, thus the insertion and removal may be improved. The guide wire 14 may be made e.g. of stainless steel or nitinol, but other materials are of course possible.

Figure 9:
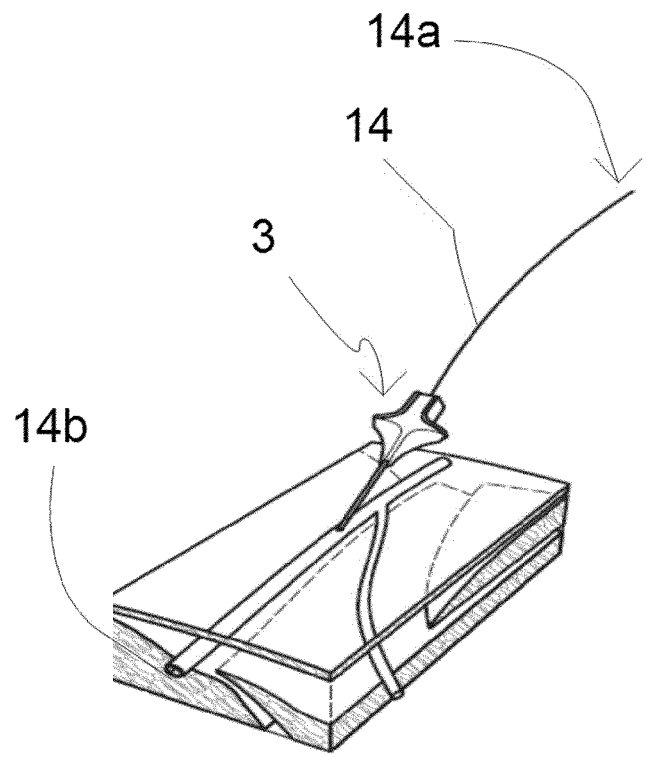

In FIG. 9, the distal end 14b of the guide wire may be inserted into the lumen of the catheter 3 with at least a portion of the guide wire protruding beyond the distal end of the flexible insertion tube 8. The user/surgeon may hold and manually maneuver the proximal end 14a of the guide wire 14, thus the guide wire 1 into the hollow organ may be properly placed. In some examples, the guide wire 14 may have a handle located at or near the proximal end 14a of the guide wire 14, thus facilitating the control of the guide wire.

Figure 10:
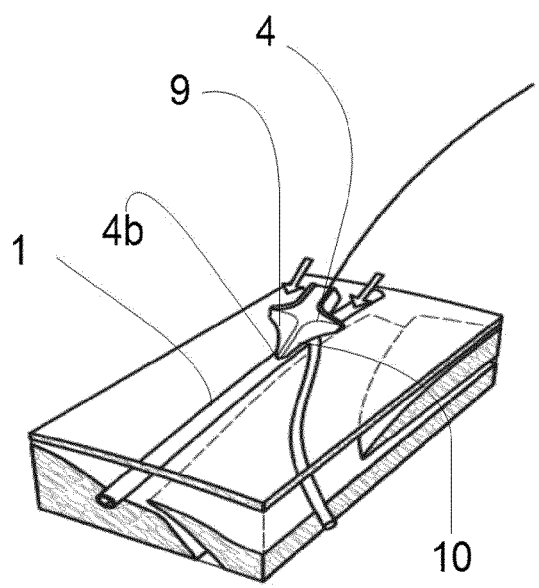

In FIG. 10, the flexible insertion tube (not shown) may be completely introduced into the hollow organ 1 by simply advancing the catheter 3 along the previously positioned guide wire. Consequently, the part of the body 4 at or near the distal end 4a of the body may also be introduced into the hollow organ 1. At this moment, the catheter device 3 may be pressed by the user/surgeon and the skin of the patient may be tightened. The first cutting edge 9 and the second cutting edge 10 may thus be introduced increase the incision of the original puncture or nick made on the skin.

Figure 11:
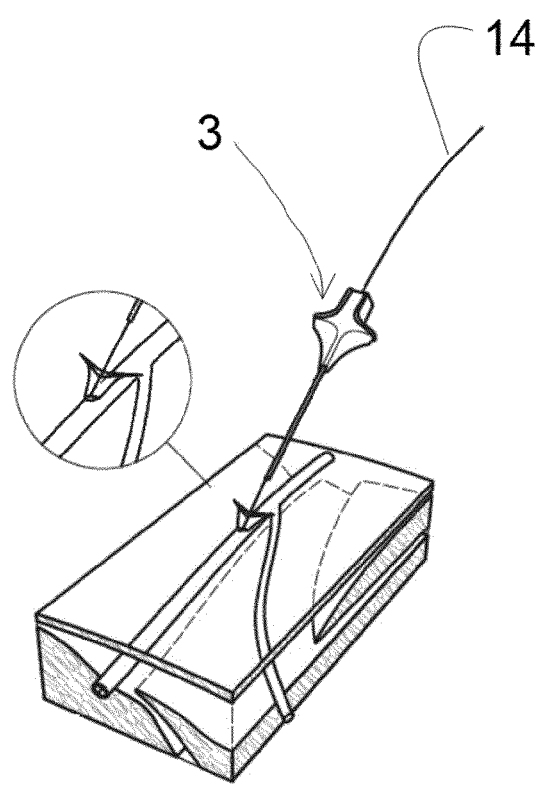

In FIG. 11, the catheter device 3 has already been introduced into the hollow organ (and thus the patient's skin) and the nick has been enlarged. The catheter device 3 may thus be withdrawn. The guide wire 14 still remains located in the vein 1. This way, the guide wire 14 may be used for the insertion of a guide catheter (not shown).

The treatment catheter may comprise a conical tapered distal portion that is narrower compared to the proximal portion of the catheter. The treatment catheter may thus act as a dilator to facilitate advancement of the treatment catheter through the hollow organ. Moreover, the treatment catheter may provide additional stiffness or reinforcement in the wall of the hollow organ. Fluoroscopy may be used to confirm the position of the catheter and to manoeuvre it to the desired location.

After completion of an intervention, the treatment catheter may be withdrawn. In some examples, a sealing device may be used to close the incision made by the procedure.

In further examples, the catheter may be operated in similar procedures without the flexible insertion tube 8. Other aspects of the catheter device (materials, sizes, dimensions, variations etc.) could be the same as in the various embodiments illustrated before. In these examples, the removable elongated needle 11 may be advanced through the internal channel of the body 4. Again, the needle could also be pre-assembled with the catheter e.g. in a pre-packaged kit.

The procedure could generally be very similar to what was shown before, except for that the guide wire would be introduced into the vein using a hollow needle. After introduction of the guide wire, the needle could be removed, and enlargement of the incision could take place similarly as in other examples, i.e. by advancing or sliding the catheter device along the guide wire.

In yet further examples, the cutting end 12 of the needle 11 could extend very slightly beyond the distal end of the channel (and thus the distal end of the body 4). As an initial puncture is made, and the needle protrudes into a patient's body, substantially immediately the original incision would thus be enlarged by the cutting edges of the catheter device. Depending on the duct or lumen that needs to be accessed, this could be useful.

If a hollow needle were used, a guide wire could be introduced through the needle. Otherwise the needle could be withdrawn, and the guide wire could be introduced through the channel in the catheter into e.g. the vein.

Although only a number of examples have been disclosed herein, other alternatives, modifications, uses and/or equivalents thereof are possible. Furthermore, all possible combinations of the described examples are also covered. Thus, the scope of the present disclosure should not be limited by particular examples, but should be determined only by a fair reading of the claims that follow.

What is claimed is:

1. A catheter device configured to provide access to a hollow organ through a puncture made in a skin of a patient comprising:
  a body having a proximal end, a distal end and a non-cylindrical external shape and a flexible insertion tube having a proximal end and a distal end, the body including one or more external flat surfaces located between the proximal and distal ends of the body wherein:
    the body comprises:
      an internal elongated channel that extends along an entire length of the body between the proximal end and the distal end of the body, wherein the internal elongated channel is configured to receive a removable elongated needle, and
      only first and second cutting edges extending rearwardly from the distal end of the body, the first and second cutting edges being located on opposite sides of the body and configured to act together to elongate the puncture when advanced into the puncture,
    the flexible insertion tube is fixedly attached to the distal end of the body and comprises:
      a tubular elongated passage aligned with the internal elongated channel of the body forming a lumen having a length.

2. The catheter device according to claim 1, wherein the first and second cutting edges are straight and are each oriented non-parallel to a longitudinal axis extending through a center of the internal elongated channel.

3. The catheter device according to claim 1, wherein each of the first and second cutting edges comprises a concaved curved surface.

4. The catheter device according to claim 1, further comprising consecutive symmetric marks provided adjacent at least one of the first and second cutting edges and being configured to indicate a length of the access into the skin of the patient.

5. The catheter device according to claim 4, wherein the marks are equidistantly spaced apart with respect to each other between 0.5 cm and 1.5 cm.

6. The catheter device according to claim 1, further comprising a grip located at or near the proximal end of the body configured to manipulate the body.

7. The catheter device according to claim 1, wherein the flexible insertion tube is made of a polytetrafluoroethylene (PTFE).

8. The catheter device according to claim 1, wherein the body is made of a polymer or mixture of polymers.

9. A kit including:
the catheter device according to claim 1, and
the elongated needle configured to be slidably inserted into the lumen of the catheter device, wherein the needle comprises a cutting end which when inserted in the lumen of the catheter device extends beyond a distal end of the lumen.

10. The kit according to claim 9, wherein the elongated needle is a hollow needle comprising a passage configured to allow an insertion and removal of a wire.

11. The kit according to claim 9, further comprising a guide wire configured to be advanced and removed through the lumen.

12. The kit according to claim 11, further comprising a treatment catheter configured to pass over the guide wire.

13. A method for accessing a hollow organ comprising:
providing the catheter device according to claim 1;
providing the elongated needle comprising a cutting end;
inserting the elongated needle in the lumen of the catheter device until the cutting end extends beyond the distal end of the flexible insertion tube of the catheter device;
making a nick in the skin of the patient and the hollow organ using the cutting end of the elongated needle while in the lumen of the catheter device;
inserting at least part of the flexible insertion tube into the hollow organ;
inserting a guide wire through the lumen of the catheter device;
increasing a length of the nick by inserting the cutting edges of the body of the catheter device into the nick.

14. The method according to claim 13, further comprising removing the catheter device over the guide wire.

15. The method according to claim 14, further comprising passing a treatment catheter over the guide wire.

16. The method according to claim 15, further comprising removing over the guide wire the treatment catheter and sealing the nick.

17. The method according to claim 13, wherein the elongated needle is a hollow needle comprising a channel.

18. The method according to claim 17, wherein the inserting the guide wire through the lumen of the catheter device comprises inserting the guide wire through the channel in the needle.

19. The method according to claim 18, further comprising withdrawing the elongated needle after inserting the guide wire through the channel of the elongated needle.

* * * * *